(12) United States Patent
Black et al.

(10) Patent No.: US 9,730,718 B2
(45) Date of Patent: Aug. 15, 2017

(54) MEDICAL DEVICE WITH QUICK-RELEASE MECHANISM

(71) Applicant: Boston Scientific Scimed, Inc., Maple Grove, MN (US)

(72) Inventors: James Black, Malibu, CA (US); Jonathan Currier, Nashua, NH (US); Paul Barner, Valencia, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 469 days.

(21) Appl. No.: 14/203,183

(22) Filed: Mar. 10, 2014

(65) Prior Publication Data

US 2014/0277044 A1 Sep. 18, 2014

Related U.S. Application Data (60) Provisional application No. 61/780,216, filed on Mar. 13, 2013.

(51) Int. Cl.
*A61B 17/29* (2006.01)
*A61B 17/00* (2006.01)

(52) U.S. Cl.
CPC .... *A61B 17/29* (2013.01); *A61B 2017/00323* (2013.01); *A61B 2017/00473* (2013.01); *A61B 2017/00477* (2013.01); *A61B 2017/2931* (2013.01)

(58) Field of Classification Search
CPC .......... A61B 17/29; A61B 2017/00318; A61B 2017/00323; A61B 2017/003; A61B 2017/2931; A61B 2017/0046; Y10T 403/60; Y10T 403/602; Y10T 403/66; Y10T 403/57; Y10T 403/7039; Y10T 403/7045
USPC ......... 606/129, 130, 205–211; 403/314, 320, 403/343, 409.1
See application file for complete search history.

(56) References Cited

U.S. PATENT DOCUMENTS

| | | | | |
|---|---|---|---|---|
| 711,284 A | * | 10/1902 | Carey | F16B 3/00 403/318 |
| 1,173,289 A | * | 2/1916 | McKee | F16H 55/06 285/417 |
| 1,438,751 A | * | 12/1922 | Des Isles | H02G 3/06 220/3.3 |
| 2,114,127 A | * | 4/1938 | Neuberth | F16B 7/22 403/331 |

(Continued)

*Primary Examiner* — Elizabeth Houston
*Assistant Examiner* — Charles Wei
(74) *Attorney, Agent, or Firm* — Bookoff McAndrews, PLLC (57) ABSTRACT

A medical device including an elongate member having a proximal end, a distal end, and at least one lumen extending therebetween. The medical device may also include at least one proximal control member extending within the elongate member from the proximal end to the distal end of the elongate member, a coupling mechanism disposed adjacent a distal portion of the elongate member, and an end-effector removably coupled to the distal end of the elongate member, wherein the end-effector includes at least one distal control member extending proximally therefrom, and wherein the coupling mechanism is configured to removably couple the at least one distal control member to the at least one proximal control member.

16 Claims, 4 Drawing Sheets

(56) References Cited

U.S. PATENT DOCUMENTS

| | | | | |
|---|---|---|---|---|
| 2,315,414 A * | 3/1943 | Germany | ............ | E21B 17/046 24/572.1 |
| 2,319,892 A * | 5/1943 | Thomas | ............ | F16D 1/04 403/286 |
| 2,465,783 A * | 3/1949 | Beaty | ............ | H01R 13/28 403/180 |
| 3,092,403 A * | 6/1963 | Gerdeman | ............ | F16L 15/006 285/330 |
| 3,873,223 A * | 3/1975 | Caperton | ............ | F16B 7/22 403/341 |
| 4,919,112 A | 4/1990 | Siegmund | | |
| 5,269,572 A * | 12/1993 | Mefferd | ............ | E21B 17/046 285/330 |
| 5,439,478 A * | 8/1995 | Palmer | ............ | A61B 1/00087 600/564 |
| 5,782,748 A * | 7/1998 | Palmer | ............ | A61B 10/06 600/104 |
| 5,950,744 A * | 9/1999 | Hughes | ............ | E21B 17/046 166/242.6 |
| 6,004,263 A | 12/1999 | Nakaichi et al. | | |
| 6,059,719 A * | 5/2000 | Yamamoto | ............ | A61B 1/00059 600/104 |
| 6,221,070 B1 | 4/2001 | Tu et al. | | |
| 6,491,627 B1 | 12/2002 | Komi | | |
| 6,578,876 B2 * | 6/2003 | Guertin, Jr. | ............ | F16L 15/00 285/148.19 |
| 6,877,927 B2 * | 4/2005 | Paulin | ............ | F16D 1/04 403/293 |
| 7,758,569 B2 | 7/2010 | Brock | | |
| 8,048,024 B2 * | 11/2011 | Tah | ............ | A61B 1/0052 604/95.04 |
| 8,048,025 B2 | 11/2011 | Barenboym et al. | | |
| 8,257,377 B2 * | 9/2012 | Wiener | ............ | A61B 17/32006 606/169 |
| 8,425,408 B2 | 4/2013 | Boulais et al. | | |
| 2006/0184161 A1 * | 8/2006 | Maahs | ............ | A61B 18/1492 606/2 |
| 2008/0243106 A1 * | 10/2008 | Coe | ............ | A61B 17/00234 606/1 |
| 2009/0137872 A1 * | 5/2009 | Bahney | ............ | A61B 1/018 600/118 |
| 2009/0209947 A1 * | 8/2009 | Gordin | ............ | A61B 1/32 606/1 |
| 2009/0227842 A1 | 9/2009 | Ando | | |
| 2010/0076266 A1 | 3/2010 | Boulais et al. | | |
| 2011/0213361 A1 | 9/2011 | Cunningham et al. | | |
| 2012/0259358 A1 * | 10/2012 | Kaercher | ............ | A61B 17/29 606/205 |
| 2012/0271347 A1 * | 10/2012 | Kaercher | ............ | A61B 17/29 606/205 |
| 2013/0023911 A1 * | 1/2013 | Esanu | ............ | A61B 17/122 606/158 |
| 2013/0053835 A1 * | 2/2013 | Bacher | ............ | A61B 17/29 606/1 |

* cited by examiner

MEDICAL DEVICE WITH QUICK-RELEASE MECHANISM

CROSS-REFERENCE TO RELATED APPLICATIONS

This application claims the benefit of priority of U.S. Provisional Application No. 61/780,216, filed on Mar. 13, 2013, the entirety of which is incorporated by reference herein.

FIELD OF THE DISCLOSURE

Embodiments of the present disclosure generally relate to medical devices and procedures. In particular, embodiments of the present disclosure relate to medical devices having a steerable portion. More specifically, embodiments of the present disclosure relate to medical devices having a removable and steerable portion, which utilize mechanisms for attaching and detaching the steerable portion to/from the steering system of a medical device.

BACKGROUND OF THE DISCLOSURE

Medical devices, such as endoscopes or other suitable introduction sheaths, are employed for a variety of diagnostic and surgical procedures, including laparoscopy, arthroscopy, gynoscopy, thoracoscopy, and cystoscopy. Such procedures may be generally carried out by inserting an introduction sheath into a patient's body through a surgical incision or via natural anatomical orifices (e.g., mouth, vagina, and/or rectum). Typically, the operator advances the introduction sheath through lumens within a patient's body, often requiring turns through tortuous vasculature and other passages. Such turns are negotiated by employing a steering mechanism.

A typical steering mechanism employs one or more steering wires extending from a handle disposed at a proximal end of a medical device. A physician can manipulate the distal portion of the medical device by manipulating the handle to push and/or pull the steering wires, which move/rotate the distal end of the device one way or the other. When assembled for use, an endoscopic device includes the operator's handle, an elongate member having a lumen extending through it, and an end-effector. The end-effector may be a tool for performing one or more surgical/diagnostic procedures, including, e.g., resectioning. Typical end-effectors include, but are not limited to, snares, forceps, graspers, scissors, needle drivers, and the like.

Unfortunately, many endoscopic devices or introduction sheaths are provided as complete units, with an articulating portion integrally formed with the remainder of the device, including the handle. In addition, many of the endoscopic devices available in the art are furnished as complete units, with the handle and elongate member permanently attached to the end-effector. Therefore, replacing an articulating portion or an end-effector in such devices is a challenge. Some devices do allow interchangeable end-effectors or articulating portions, however, most of those devices often require complete replacement of the steering or actuating mechanisms during the process of replacement of the articulating portion or end-effectors, which may be a substantially labor intensive, costly, and complicated task.

Therefore, there remains a need for a system that allows for more easy and convenient interchange of end-effectors and/or articulating distal portions.

SUMMARY OF THE DISCLOSURE

Embodiments of the present disclosure relate to a device for detaching and/or reattaching an articulating distal end or an end-effector to a steering and/or actuating mechanisms of a medical device.

In one embodiment, a medical device may include an elongate member having a proximal end, a distal end, and at least one lumen extending therebetween. The medical device may also include at least one proximal control member extending within the elongate member from the proximal end to the distal end of the elongate member, a coupling mechanism disposed adjacent a distal portion of the elongate member, and an end-effector removably coupled to the distal end of the elongate member, wherein the end-effector includes at least one distal control member extending proximally therefrom, and wherein the coupling mechanism is configured to removably couple the at least one distal control member to the at least one proximal control member.

Various embodiments of the medical device may include one or more of the following features: a handle operably coupled to the proximal end of the elongate member; when the proximal control member and distal control member are removably coupled together, the proximal control member and distal control member are configured to cooperatively actuate the end-effector; a proximal end portion of the distal control member includes a first structure; a distal end portion of the proximal control member includes a second structure different from the first structure; one of the first and second structures is configured to receive the other of the first and second structures; the first structure includes a hook-like configuration, and the second structure includes an opening configured to receive the hook-like configuration; the coupling mechanism includes a plurality of plates, wherein at least one plate includes an opening for receiving the proximal control member therein; one of the plurality of plates is movable relative to the other of the plurality of plates; a resilient member is operably coupled to at least one of the plurality of plates; one of the plurality of plates is operably coupled to a cam; at least one proximal control member includes a plurality of proximal control members, and the at least one distal control member includes a plurality of distal control members.

A medical device including an elongate member including a proximal end, a distal end, and a lumen extending therebetween, wherein a handle is operably coupled to the proximal end. The medical device may also include a plurality of control members extending within the lumen from the handle to the distal end of the elongate member, a coupling mechanism disposed adjacent the distal end of the elongate member, wherein the coupling mechanism includes a plurality of plates, and wherein one of the plurality of plates is movable relative to the other of the plurality of plates, and an end-effector removably coupled to the distal end of the elongate member, wherein the end-effector includes a plurality of distal control members extending proximally therefrom.

Various embodiments of the medical device may include one or more of the following features: the coupling mechanism is configured to operably couple each of the plurality of control members to corresponding distal control members; at least one of the plurality of plates is coupled to a resilient member; at least one of the plurality of plates is operably coupled to a cam; and a proximal end portion of at least one of the plurality of distal control members includes a first structure, and wherein a distal end portion of at least one of the plurality of control members includes a second structure different from the first structure.

In another embodiment, a method of replacing an end-effector of an endoscopic medical device may include decoupling the end-effector from a distal portion of an elongate member, wherein decoupling the end-effector includes disengaging at least one distal control member from a proximal control member. The method may also include coupling a second end-effector to the distal portion of the elongate member, wherein coupling the second includes coupling a control member extending proximally from the second end-effector to the proximal control member.

Various embodiments of the medical device may include one or more of the following features: the end-effector may be a disposable end-effector; and decoupling the end-effector from the distal portion of an elongate member includes moving one of the end-effector or the elongate member towards one another.

Additional objects and advantages of the described embodiments will be set forth in part in the description that follows, and in part will be obvious from the description, or, may be learned by practicing the disclosure. The objects and advantages of the disclosure will be realized and attained by means of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The accompanying drawings, which are incorporated in, and constitute a part of this specification, illustrate exemplary embodiments of the present disclosure and, together with the description, serve to explain the principles of the disclosure.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts.

Overview

As alluded to above, many medical devices include an elongate member defining one or more lumens extending through that member. A proximal end of the elongate member may be operably connected to a handle, and a distal end thereof may be operably coupled to a suitable end-effector. A steering mechanism may extend from the handle to the end-effector, through the elongate member, and may be operably coupled to controls on the handle. The steering mechanism may allow an operator to articulate or rotate a distal portion of the elongate member.

Embodiments of the present disclosure relate to mechanisms that allow replacement/detachment of a distal portion of a medical device. For instance, a mechanism of the present disclosure may include a device to detach and/or reattach an end-effector (e.g., a disposable end-effector) to the distal end of an elongate member of a medical device. In addition, the described mechanism may allow for detaching and attaching a distal articulating portion of a medical device. Specifically, a steering mechanism may extend through the elongate member, and may be configured to steer the elongate member and/or control an end-effector associated with a distal portion of the medical device. The steering mechanism may facilitate connection/disconnection of the steering mechanism to the distal portion, including, e.g., an end-effector. Examples of suitable end-effectors may include, though not limited to, scissors, biopsy forceps, dilators, lithotripters, or the like. Various configurations of the device articulation, structure, and function are described in the embodiments of the disclosure. Further, as used in this disclosure, "distal" refers to a position or direction away from a user, and "proximal" refers to a position or direction opposite the "distal" direction, and closer to the user (i.e., towards the user).

In some embodiments, the device may employ a coupling unit to operably attach or detach an attachment member (e.g., an end-effector) to the distal end of a medical device, such as an endoscopic medical device. The coupling unit may include a proximal component and a distal component configured to transition between a connected configuration and a disconnected configuration. Further, the proximal component of the coupling unit may be operably attached to a distal end of, e.g., an elongate member of the medical device, while the distal component of the coupling unit may connect to a proximal portion of an end-effector.

Exemplary Embodiments

Figure 1A:
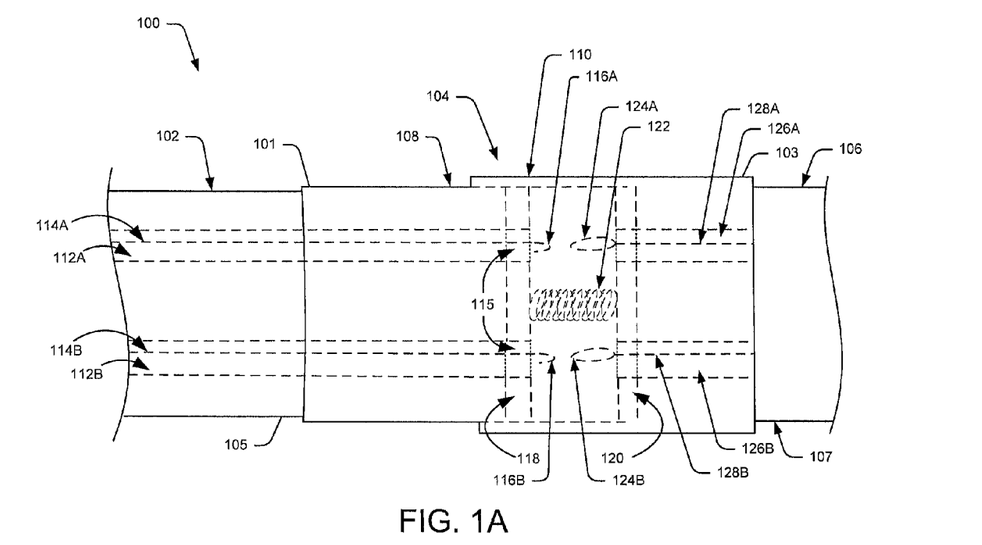
FIG. 1A is a sectional view of an exemplary connection system in a disconnected configuration, according to an embodiment of the present disclosure.
Figure 1B:
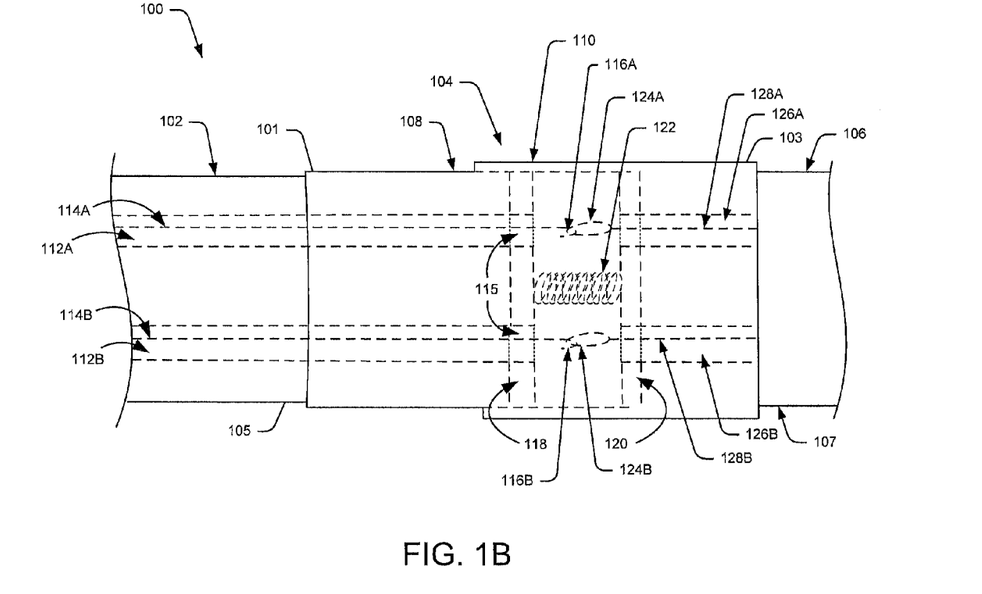
FIG. 1B illustrates the system of FIG. 1A in a connected configuration.

FIGS. 1A and 1B depict sectional views of an exemplary connection system 100, according to an embodiment of the present disclosure. The system 100 may be adapted to provide a detachable connection between two portions of a steerable device. For instance, as depicted in the present embodiment, the system 100 may be employed to detachably connect an attachment member 106, to an elongate member 102 of a medical device. In particular, the term "elongate member" as used herein, may refer to a variety of delivery devices capable of being introduced through a body lumen, either alone or in combination with one or more medical device, to accomplish a variety of diagnostic and/or therapeutic procedures.

The system 100 may further include a coupling unit 104 for detachably connecting the elongate member 102 to the attachment member 106. The coupling unit 104 may be positioned between the elongate member 102 and the attachment member 106, and it may have a proximal portion 101 and a distal portion 103. The proximal portion 101 may be coupled to a distal end 105 of the elongate member 102, and the distal portion 103 may couple to a proximal end 107 of the attachment member 106. The proximal portion 101 and the distal portion 103 may either be integral components of the coupling unit 104, thus, constituting a consolidated body/assembly, or may also be two different pieces secured and fused to two ends of the coupling unit 104. In a case where two separate pieces are attached to the ends of the coupling unit 104, any appropriate mechanism can be used to secure the pieces to the coupling unit 104, e.g., welding the pieces, or adhesively bonding them to the ends of the coupling unit 104. Moreover, the ends of the coupling unit 104 may be internally threaded, and the proximal portion 101 and the distal portion 103 of the coupling unit 104 may have threaded outer portions, to facilitate securing of these portions to the ends of the coupling unit 104.

Further, as shown in FIG. 1A, a distal end of the elongate member 102 may be positioned to be coupled to the proximal end of the attachment member 106. As used herein, "attachment member" may be either an end-effector, including the entire range of end effector elements, such as forceps, snares, cutting devices, and so on, or any steerable element that becomes useful by attachment to the distal end of a medical device. Further, a medical device may be an endoscopic device, Illumination devices, a visualization device, an imaging device and the like. Multiple channels, for example, channels 112A and 112B, as depicted, are provided within the elongate member 102. Each such channel may extend along the entire length of the elongate member 102. Specifically, each channel may extend from a proximal edge to a distal edge of the elongate member 102, and may lead into the coupling unit 104. The channels 112 may have a circular cross-section or any other appropriate cross-sectional shape, e.g., square cross-section, rectangular cross-section, etc., thus, not limiting the scope of the present disclosure. Each channel 112 is coated with a suitable material, to avoid its outer portion from abrading. Any appropriate coating material can be used for that purpose.

A set of control members 114, i.e., control members 114A and 114B, as shown, are disposed within each of the channels 112. These control members 114 may be wires, braided wires, rods, etc. Each control member 114 may pass through one of the channels 112, and may have its distal end extending outwards from that channel. Further, in an embodiment, more than one control member 114 may also extend and pass through each channel 112. The distal end of each control member 114 may be detachably coupled to a coupling mechanism provided within the coupling unit 104. The coupling mechanism will be described in further details hereinafter. The outer surface of each of the control members 114 may be coated with an appropriate material, to prevent their abrasion, due to being in contact with the inner surface of the channels 112.

As known in the art, a proximal end (i.e., left side end in the depicted configuration) of each control member 114 may be connected to a handle (not shown) of the endoscopic device, and the handle may be driven by control elements (not shown), for steering and actuating an end-effector or other element of attachment member 106 through the control members 114. Therefore, the control members 114 may act as steering wires for steering the attachment member 106 (e.g., the end-effector) attached to the distal portion of the system 100. Optionally, the medical device may include a braking member (not shown), which may be releasably engaged with the control members 114, to prevent the control members 114 from moving through the channels 112, until the braking member is released. The distal ends of the control members 114A and 114B may form into male coupling members, such as hooks 116A and 116B, respectively, (collectively, hooks 116) and these hooks may selectively extend beyond the distal end of elongate member 102.

The distal portion 103 of the coupling unit 104 may be attached to a proximal end of attachment member 106. Further, the distal portion 103 may also be integrally fused to the attachment member 106. Specifically, the distal portion 103 and the attachment member 106 may also be integral portions of a consolidated body. In an embodiment, an end cap 121 of substantially cylindrical cross-section may be provided at a distal end of the coupling unit 104. A distal end of the end cap 121 may be configured to receive a proximal end of the attachment member 106 to facilitate engagement of the coupling unit 104 with the attachment member 106.

Multiple channels 126A and 126B, as shown, may be provided within the attachment member 106, and each such channel may extend through the entire longitudinal length of the attachment member 106. Wherever mentioned collectively hereinafter, the channels 126A and 126B will be simply referred to as 'channels 126' for simplicity and economy of expression. The channels 126 may have a circular cross-section. However, other appropriate alternative cross-sectional shapes may also be contemplated, for example, square cross-section, rectangular cross-section, etc., and hence, the depicted shape is not intended to limit the scope of the present disclosure.

Elongate member 102 and attachment member 106 are positioned in a manner that each of the channels 112 provided within, and extending through the elongate member 102 substantially aligns with one or more of the channels 126 provided within the attachment member 106. For example, as shown, the channel 112A is positioned at the same horizontal level as the channel 126A, so as to facilitate proper alignment of those two channels. Distal control members 128A and 128B (collectively referred to as 'distal control members 128') may be disposed within channels 126. Each of the distal members 128 may be in the form of a wire, a braided wire, or a rod, etc. Further, these distal control members 128 may extend till the distal portion (not shown) of attachment member 106, and, may be coupled to an operational mechanism at their distal ends. The operational mechanism may be a steering mechanism or the actuating mechanism for an end-effector, as known in the art. Though only two distal control members, i.e., 128A and 128B have been shown, it is contemplated that multiple such control members may be provided, and each such distal control member may extend through a specific channel 126 provided within the attachment member 106. Further, some embodiments of the present disclosure may also incorporate provision of more than one distal control member 128 extending through each channel 126.

The channels 112A and 112B may be in the form of cylindrical lumens, or may also any other appropriate cross section. Further, the channels extend and cover the entire length of first component 108. The control members 114A and 114B, as described earlier, pass through these channels 112. These members 114, as shown, are positioned within the channels 112 in a manner aligning substantially parallel to the longitudinal length of the channels 112.

In some embodiments, a braking member (not shown) may releasably engage the distal control members 128, to prevent the distal control members 128 from sliding within channels 126, until the braking member is released. The proximal end of each distal control member 128 may be formed into a female coupling member, such as loops 124, which may extend beyond the proximal end of attachment member 106. Of course, the proximal end of each distal control member may include a male coupling member for mating with a corresponding female coupling member. Further, the coupling members may include any suitable configuration and are not limited to the male/female configurations. The loops 124A and 124B may be circular, ovular, arcuate, or may have another other appropriate shape.

In an embodiment, the male coupling members 116 provided at the distal end of the control members 114, and the female coupling members 124 provided at the proximal ends of the distal control members 128, are operably switchable or reversible, i.e., the coupling members 116 may act as female coupling members, and the coupling members 124 may act as male coupling members. Specifically, a loop-shaped structure (acting as a female coupling member) may be provided at the distal end of the each control member 114, and a hook-shaped structure (acting as a male coupling member) may be provided at the proximal end of each distal control member 128. Further, in another embodiment, multiple distal control members 128 may be provided, where the proximal ends of some of those distal control members may be formed into female coupling member, and the proximal ends of some may be formed into male coupling members. Those female and male coupling members at the proximal ends of different distal control members 128 may engage with corresponding male and female coupling members, respectively, provided at the distal ends of the control members 116.

Any other suitable coupling mechanisms may also be used for coupling the control members 116 to the control members 128, including, threaded collars, turnbuckles, and luer locks, thus not limiting the scope of the present disclosure.

Figure 2A:
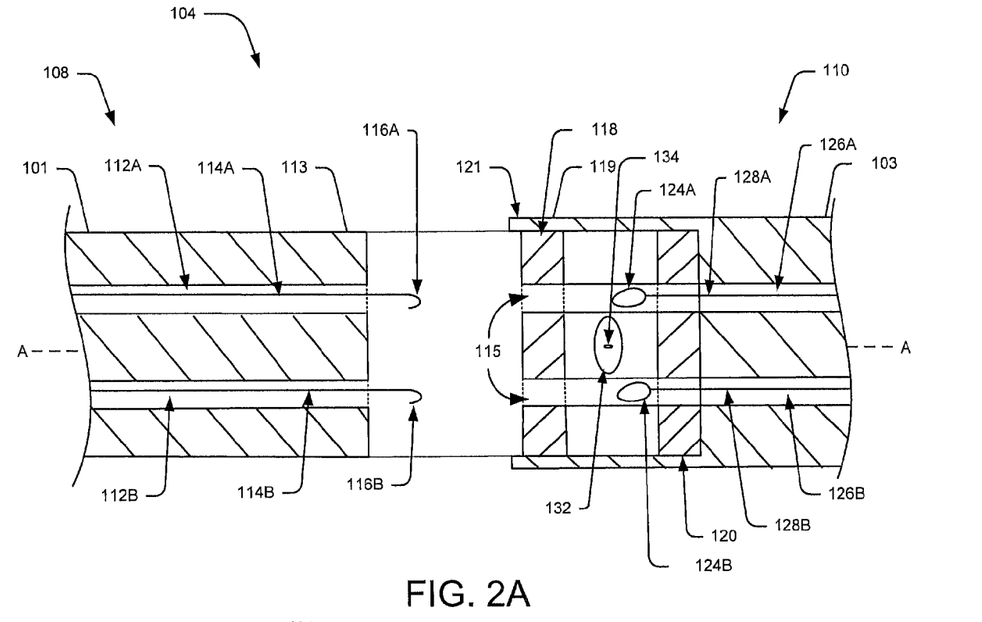
FIG. 2A is a sectional view of another embodiment of a connection system of the present disclosure.
Figure 2B:
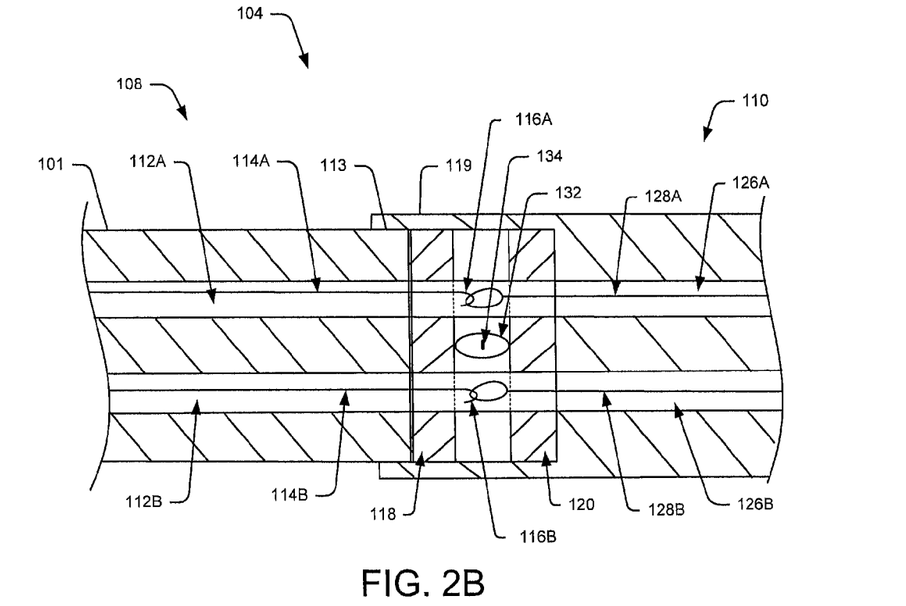
FIG. 2B is a sectional view of the system of FIG. 2A in a connected configuration.

In some embodiments, the distal portion 103 of coupling unit 104 may include a movable plate 118 and a stationary plate 120, disposed at the proximal end of attachment member 106, as shown in FIGS. 2A-2B. The plates 118 and 120 may be disposed within end cap 121. These plates may be sized to span the entire interior cross-sectional portion of the end cap 121. The stationary plate 120 may be pressed snugly against the proximal end of the attachment member 106. In some embodiments, the stationary plate 120 may be fixedly secured to a proximal end of the attachment member 106. The movable plate 118 may be configured to move by sliding within the interior portion of end cap 121.

Figure 3A:
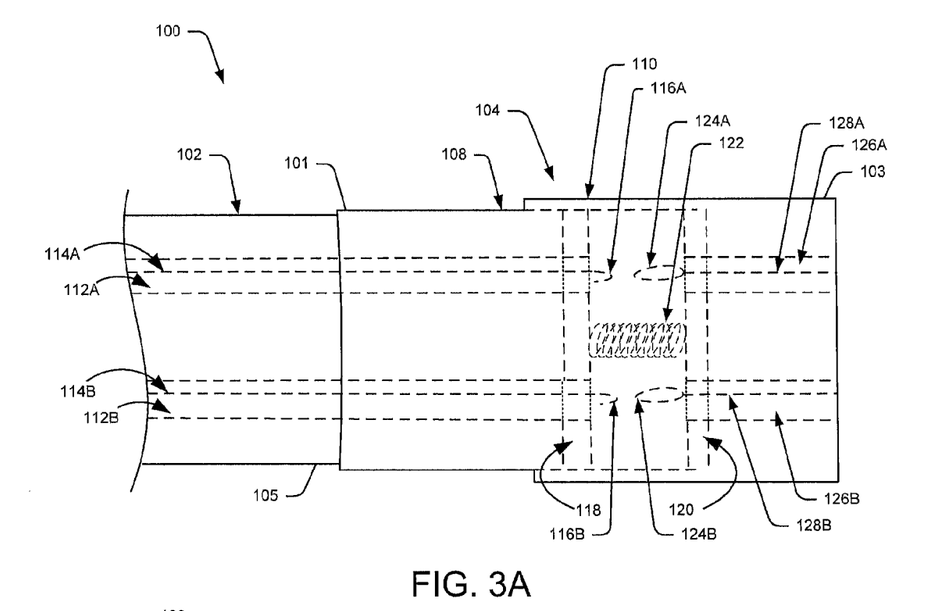
FIG. 3A is a sectional view of a steering mechanism in a decoupled configuration, configured to couple/decouple multiple steering wires to a steerable end of a medical device, in accordance with an embodiment of the present disclosure.

The plates may be connected to each other through a resilient member, such as, e.g., coil spring 122, as shown in FIG. 3A. The coil spring 122 may have one end connected to either of the plates 118 and 120, and the other end being left free. Specifically, a distal end of the coil spring 122 may be connected to the stationary plate 120, and its proximal end may be left free to contact the movable plate 118, as the movable plate 118 slides distally. The coil spring 122 may be capable of developing enough compressive force during its compression, when its free end gets in contact with the movable plate 118, to maintain a certain minimum separation between the two plates, at all points of time. Due to this virtue and design characteristic of the spring 122, a cavity or space 117 is always defined, and interposed between the movable plate 118 and the stationary plate 120. Specifically, the spring 122 may have a certain minimum stiffness constant or exert a biasing force, to maintain a minimum separation between the two plates, at all times. The spring 112 can also be replaced with any suitable resilient/elastomeric material, which may push and retract the movable plate 118 as a contact establishes.

In some embodiments, each of the plates 118 and 120 may be disc-shaped, and, may be formed of any appropriate material, such as, a metallic material, a polymer, an alloy, a composite or the like. Both the plates 118 and 120 may be provided with apertures 115, which may be holes extending through the entire cross-section of the plates, and provided at the same elevation as the channels 112 and 126 to align with them. Through these apertures 115, the coupling members 116 may be configured to access the coupling members 124, in response to movement of the proximal portion 101 with respect to the distal portion 103 of the coupling unit 104.

The mechanism for coupling the elongate member 102 to the attachment member 106, is now described in detail, in conjunction with FIG. 1B. First, the elongate member 102 is pushed distally towards the attachment member 106. In response, having its cross-section smaller than the interior cross-section of the end cap 121, the elongate member 102 enters into the end cap 121, and starts pushing against the movable plate 118. The movable plate 118 starts sliding distally, towards the stationary plate 120. Gradually, the movable plate 118 may come in contact with the free end of the coil spring 122, and may start compressing it. In some embodiments, however, plate 118 may already be in contact with coil spring 122. Effectively, the male coupling members (i.e., the hooks 116) pass through apertures 115 within the plate 118, approach the female coupling member 124 (i.e., loops 124), and engage with them. Once the engagement occurs, the elongate member is released from being pushed any further, and the coil spring 122 comes in action. Being compressed due to the earlier rightward movement of the movable plate 118, the coil spring 122 develops a sufficient restoring force, and pushes the plate 118 towards the left direction (i.e., the proximal direction). In response, the plate 118, being in contact with the elongate member 102, pushes it towards the left, and shifts it proximally. The engaged hooks 116 pull the loops 124, and stretch them. Eventually, the proximal control members 114 and the distal control members 128 develop tensions therein. The compressive force of the coil spring 122 continuously acts over the movable plate, keeps the control members 112 and 128 in tension, and therefore, keeps the hooks 116 engaged with loops 126, thus, coupling and securing the elongate member 102 to the end effector 106. The developed tension in control members 112 and 128 is necessarily for effective operation.

Additionally, in certain embodiments, a locking mechanism may be provided, to temporarily retain engagement of the hooks 116 with loops 128. This may facilitate continued coupling of the elongate member 102 to the attachment member 106, as desired. Such a locking mechanism may prevent unintended/undesirable disengagement of the elongate member 102 from the attachment member 106. The locking mechanism may include a pin engaging a slot, threaded collars, or turnbuckles, etc.

For decoupling elongate member 102 from the attachment member 106, the elongate member 102 is again moved towards the right direction (i.e., distally). The movement of the member 102 pushes the plate 118, compressing the coil spring 122. This disengages the hooks 116 from the loops 124, momentarily. The disengaged hooks 116 and the loops 124 may be brought at different vertical levels, through a suitable mechanism (not shown) to facilitate their permanent detachment from each other. Once being at different vertical levels, the elongate member 102 is freed, and the compressed coil spring 122, pushes the rightward shifted movable plate 118, retracting it towards the left direction. This pushes the elongate member 102 towards the left, shifts it along the proximal direction, and gradually decouples the elongate member 102 from the attachment member 106.

Those skilled in the art will appreciate that the attachment member 106, the elongate member 102, and the other collaborative components of the described system, including the control members the plates within the coupling unit, etc., are merely representative of the environment in which the system of the present disclosure operates. Hence, a variety of alternatively shaped collaborating components may also be used as a substitutive, for the purpose of replacing an end-effector of a medical device, thus, not limiting the scope of the present disclosure. Further, the system 100 described herein may be used to detach and/or attach a variety of end-effectors. Exemplary end-effectors may include biopsy forceps, scissors, lithotripters, dilators, other cautery tools, and the like.

Further, while system 100 is generally described with respect to the coupling unit 104 having the proximal portion 101 attached to the elongate member 102 and the distal portion 103 coupled to the attachment member 106, a variety of other configurations may also be contemplated. In addition, the methods and devices described herein are equally applicable to any configuration where an attachment member 106 may be detachably coupled to the elongate member 102.

FIG. 2A depicts a cross sectional view of the components 108 & 110 of the coupling unit 104 disassembled from each other. As with the previous embodiment, the first component 108 is configured to be attached to the distal end of the elongate member 102 (not shown), and the second component 110 is connectable to the proximal end of the attachment member 106 (not shown herein).

In the depicted embodiment, a cam 132 may be positioned between the moving plate 118 and the stationary plate 120. Although not shown, a resilient member be also provided with the cam 132. The resilient member may be similar to coil spring 122. In an embodiment, the cam 132 may have an elliptical-shaped configuration. However, other appropriate shapes for the cam 132, such as circular, polygonal, irregular, and the like may also be contemplated. The cam 132 may be secured to a suitable camshaft 134. Further, the cam 132 is configured to rotate along with the camshaft 134, between the movable plate 118 and the stationary plate 120, in the space 117 defined between the two plates. When the proximal portion 108 moves distally with respect to the distal portion 120 of the coupling unit 104, the cam 132 may rotate automatically, as the movable plate 118 slides distally towards the stationary plate 120, and makes contact with the cam 132. A torsional spring (not shown) may be attached to the camshaft 132, and the spring may wind and develop torsion in response to the rotation of the cam 132. Once enough torsion has been developed in the torsional spring, the cam may be urged to rotate oppositely, and this may push the movable plate 118 backwards. Further, in some embodiments, the rotation of the cam 132 may also be actuated manually, for example, through a rotatable knob coupled to the cam 132.

In some embodiments, the plates 118 and 120 are disc-shaped, formed of materials that may include metals, polymers, alloys, composite, or the like. Both plates 118 and 120 have apertures 115 extending through them, positioned for alignment with channels 112 and channels 126, to facilitate male coupling members, such as hooks 116 to access female coupling members, such as loops 124, whenever intended.

FIG. 2B shows a configuration where the first component 108 of the coupling unit 104 is coupled to the second component 110. The coupling is accomplished by applying a force along the distal direction to press the first component 108 against the movable plate 118. This slides movable plate 118 towards the right direction (e.g., distally) into the space 117, against the proximately oriented force of the cam 132 mounted on the camshaft 134. As mentioned earlier, the proximally orientated force developed in the cam 132 may be by virtue of a torsional spring or any other suitable mechanism connected to the camshaft 134 (not shown). When distal end of the first component 108 presses against the movable plate 118, hooks 116 extend into and through apertures 115 in movable plate 118. As movable plate 118 moves distally, the hooks 116 approach and ultimately enter the area of the loops 124. When this occurs, the distal force on the first component 108 is released. As soon as the force is released, the cam 132 rotates in anti-clockwise direction, to push the moving plate 118 back to its original location. Effectively, the cam 132 pushes movable plate 118, and in turn, the first component 108 proximally. As the hooks 116 have fallen into the area of the loops 124, the proximal movement of the first component 108 eventually engages these hooks 116 with the loops 124. Further, the control members 112 pull the control members 126, applying a tensile force thereon. Effectively, this develops a tension in both the control members 114 and 126, and tightens the engagement of the hooks 116 with the loops 124. This couples the first component 108 to the second component 110.

In addition to being held in position by the tensile force applied to control members 114 and 128, some embodiments may provide a locking mechanism to assist in maintaining engagement of the first component 108 to the second component 110. Such a mechanism would allow for continued application of longitudinally directed force between the two components, thus, preventing unintended disengagement of those components.

For decoupling the second component 110 from the first component 108, a force along the proximal direction is reapplied on the first component 108, to slide the first component 108 towards the second component 110. The movable plate 118 contacts the cam 132 and rotates it. Due to the applied force, the tension developed in the control members 114 and 128 decreases and they get slacked, and the hooks 116 are pushed into the area enclosed by the loops 124. Gradually, being pushed, the hooks 116 leave contact with the loops 124. Thereafter, an appropriate mechanism is used to pull the hooks 116 upwards, such that they misalign with the plane of the loop 124. Once that happens, the rotated cam 132 pushes the movable plate 118 backwards, and this allows the first component 108 and the hooks 116 to retract simultaneously. Eventually, with the retraction, the hooks 116 and the loops 124 disengage with each other, and this decouples the first component 108 from the second component 110.

In some embodiments, a mechanism for selectively orienting one or more of coupling members (e.g., hooks 116 and/or loops 124) relative to one another may be provided. For example, it is contemplated that the mechanism may rotated or other move one or both of hooks 116 and loops 124 into suitable engagement with another. In embodiments where the coupling members include threaded configurations, the contemplated mechanism may be used to rotate mating coupling members relative to one another.

Advantageously, the cam's incorporation facilitates a certain distance between the movable plate 118 and a stationary plate 120 to be maintained at all times, which may enable a positive engagement/disengagement between the components 108 and 110. Instead, in a case where a coil spring is used in place of cam, as described earlier, the minimum distance between the two plates 118 and 120 may change over time because of the possibility of fatigue, change in the spring co-efficient, etc., observed in a spring. Further, an incorporation of both the cam 132 and the coil spring 122 into a single connection assembly of a generic medical device may be conceivable as well.

The material used to manufacture the first component 108 and the second component 110 may include a rigid and/or a flexible material either in combination or alone. Exemplary materials may include metals, polymers, alloys, composite, or the like. In some embodiments, the material employed may include a self-expandable material such as a shape memory material, Nitinol, for example. Those skilled in the art will appreciate that any other suitable material may also be contemplated, without departing from the scope and spirit of the disclosure.

As depicted in present embodiment, the distal end 113 of the first component 108 may face the proximal end 119 of the second component 110; however, those skilled in the art will understand that any suitable arrangement of the first component 108 to the second component 110 may also be contemplated. Further, the currently depicted configuration may also be reversed in an embodiment, wherein the first component 108 may be positioned along the right side (distally from the user), and attached to an end-effector, and the second component 110 may be positioned along the left (proximal to the user) and attached to a suitable steering mechanism for operating the medical device.

Figure 3B:
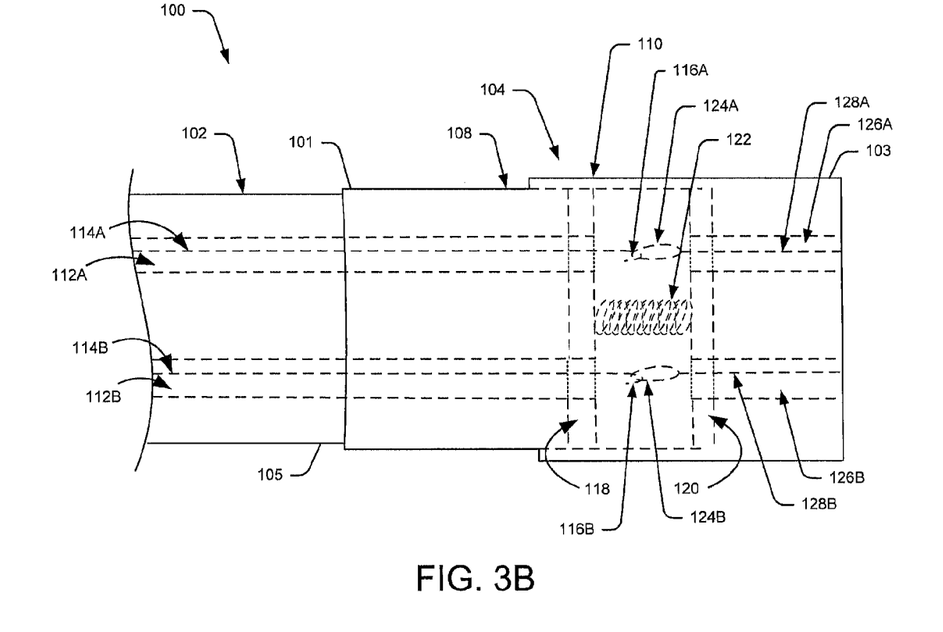
FIG. 3B depicts the steering mechanism of FIG. 3B in a coupled configuration, illustrating multiple steering wires coupled to a steerable end of a medical device.

FIGS. 3A and 3B depict sectional views of a steering mechanism for coupling or decoupling multiple steering wires to a steerable distal end of a medical device, in accordance with another embodiment of the present disclosure. Specifically, FIG. 3A depicts the mechanism in a decoupled configuration, where, the steering wires are decoupled from the steerable end. FIG. 3B depicts the steerable wires being coupled to the steerable end of the medical device.

As shown in FIG. 3A, the elongate member 102 has a distal portion coupled to the proximal portion 101 of the coupling unit 104. The distal end 103 of the coupling unit 104 may act as a steerable end, where a suitable end-effector (not shown) as mentioned earlier is configured to be attached and steered through the mechanism. Alternatively, distal end 103 may be suitably coupled to an articulating portion. The proximal control members 114, passing through and extending along the channels 112 of the elongate member 102, act as proximal steering wires in the shown embodiment. Specifically, these control members 114 are configured to steer an end-effector and/or articulating portion. The distal ends of the control members 114 may form as male coupling members, for example, hooks 116A and 116B, as shown herein, and described earlier. Further, multiple distal control members 128 extend through the distal channels 126. Each of the distal channel 126 extends through the longitudinal length of the second component 110 of the coupling unit 104. The openings of the proximal channels 112 and the distal channel 126 substantially align with each other, to facilitate engagement of the proximal control members 114 with the distal control members 128. The proximal portions of the distal control members 128 form as female coupling members, i.e., loops 124. The distal portion of the each of the distal control members 128 is configured to be coupled and attached to the end-effector or articulating portion. Acting in collaboration, the proximal control members 114 and the distal control members 128 act as steering wires configured to attach or detach and end-effector or articulating portion to the distal end 103 of the coupling unit 104. Specifically, when the two sets of control members are tensed, the end-effector is intact and fixedly connected to the distal end 103 of the coupling unit 104. Similarly, when the control members 114 and 128 are slack/de-tensioned, the end-effector gets detached from the distal end 103, and can be removed/replaced.

The means and mechanism for articulating the distal end 103, and for steering, attaching and detaching the end-effector coupled to the distal end 103 of the coupling unit 104 is now described. A pushing force is applied along the distal direction, to move the first component 108 of the coupling unit 104 distally. In the same manner as discussed earlier, the applied force moves the movable plate 118 towards the stationary plate 120. Eventually, the movable plate 118 establishes contact with the coil spring 122 disposed between the two plates, and compresses it. With the movement of the movable plate 118, the male coupling members, i.e., the hooks 116 reach in vicinity of the female coupling members, e.g., the loops 124, and engage the loops 124. When this occurs, the force applied on the first component 108 of the coupling unit 104 is released. When the applied force is released, the movable plate 118 is automatically pushed backwards, along the proximal direction, due to enough compressive force developed in the coil spring 122. Due to this, both the proximal control members 114 and the distal control member 128 develop tension, and eventually get coupled to each other. Since the distal end of the distal control members 128 is attached to a suitable end-effector, effectively, the end-effector gets coupled/attached to the mechanism in that configuration. Specifically, that engagement of the proximal control members (acting as proximal steering wires) with the distal control members (acting as distal steering wires) couples the end-effector to the medical device.

In FIG. 3B, the two sets of steering wires, i.e., the proximal control members 114 and the distal control members 128 are shown coupled to each other. As depicted, the hooks 116 at the distal end of each proximal control member 114 engage the loops 128 at the proximal end of a specific distal control member. Further, the two sets of control members are taut, and have developed sufficient tension in the shown configuration.

The proximal control members 114 may be used to control and steer the distal end 103 of the coupling unit 104 (or, effectively, the end-effector/surgical tool attached to the distal end). To facilitate this, the proximal end of each proximal control member may be attached to a proximal handle (not shown). Specifically, when the handle is operated, the proximal control members 114 may act as steering wires, which may steer an end-effector or an articulating portion. Movement of the proximal control members 114 in up/down direction, or precise pushing/pulling of the control members 114 may accordingly move (including, e.g., rotate) and position the end-effector/articulating portion in an intended configuration.

To detach and decouple the end-effector from the medical device, the proximal steering wires (i.e., the proximal control members 114) need to be decoupled from the distal steering wires (i.e., the distal control members 128). Similar steps, as mentioned earlier, may be used to detach the two sets of control members from one another. Specifically, the first components 108 of the coupling unit 104 may be again pushed distally, to allow the movable plate 118 to slide towards the stationary plate 120. This compresses the coil spring 122, and eventually loosens the engagement of the hooks 116 with the loops 124 momentarily. Once that happens, to facilitate permanent disengagement, the hooks 116 are misaligned from the plane of the loops 124 through a suitable mechanism (though not shown). The force applied on the first component 108 is then withdrawn, and the compressed coil spring 122 pushes the movable plate 118 and retracts it backwards. This eventually moves the first component 104 along the proximal direction, and detaches the distal steering wires (i.e. distal control members 128) from the proximal steering wires (i.e., proximal control members 114). Effectively, the end-effector, earlier attached to the distal portion of the coupling unit 104, now gets detached from the medical device, and can be removed or replaced.

Embodiments of the present disclosure may also incorporate use of a cam disposed between the movable plate 118 and the stationary plate 120, instead of the coil spring 122, as illustrated in FIG. 2B earlier, and described in conjunction therewith. In those embodiments, the tensioning/de-tensioning of the steering wires, to couple and decouple an end-effector remains substantially similar as described earlier, and will not be discussed again to avoid unnecessary repetition.

Figure 4A:
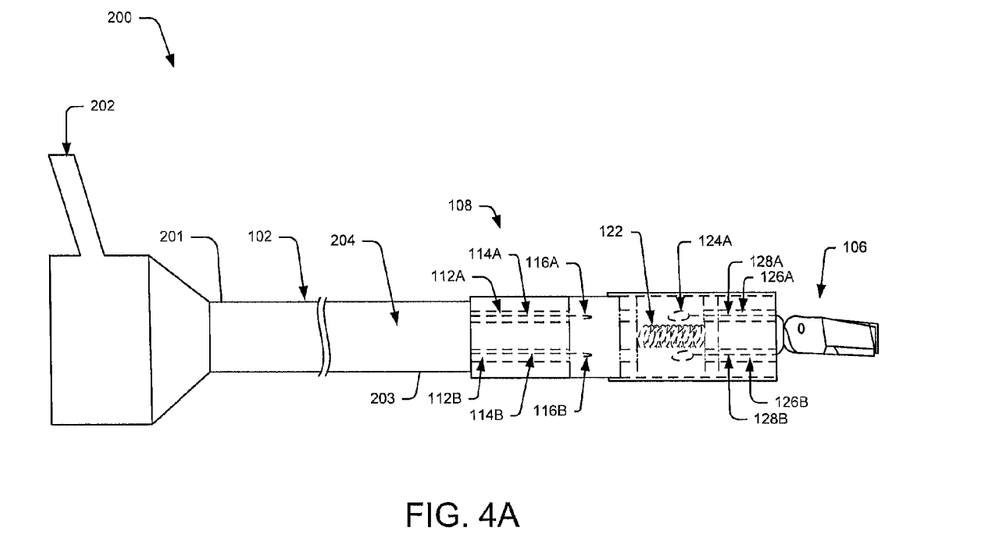
FIG. 4A is an exemplary medical device, incorporating the connection system of FIG. 1A, showing the connecting system in a disassembled configuration, in accordance with an aspect of the present disclosure.

FIG. 4A shows a medical device 200 incorporating the connection system 100 of FIG. 1, according to an embodiment of the disclosure. The medical device 200 may include a handle 202, operably connected to a proximal end 201 of the elongate member 102. The elongate member 102 may be a catheter, sheath, a cannula, etc. The coupling unit 104 may be disposed between the elongate member 102 and an end-effector 106. The first component 108 of the coupling unit 104 may be disposed at a distal end 203 of the elongate member 102. Further, as shown, the end-effector 106 is detachably coupled to the distal end 203 of the elongate member 102, through the coupling unit 104.

The elongate member 102 may include an introduction sheath, which may be flexible or rigid, adapted to be easily inserted into a body lumen. In general, the elongate member 102 may include a tube-like configuration having a circular cross-section. However, other cross-sectional shapes may also be contemplated, such as elliptical, oval, polygonal, or an irregular cross-section. In addition, the cross-sectional configuration of the elongate member 102 may be uniform along its length, or may also vary. For instance, the distal end 203 of the elongate member 102 may be tapered relative to the proximal end 201, facilitating convenient insertion of the elongate member 102 within a body lumen.

The handle 202 may include a mechanism (not shown) to operate the end-effector 106 disposed at the distal end of the medical device 200. Specifically, to accomplish distal operation of the end-effector 106, through the handle 202, one or more actuating members 114a may extend through a lumen 204 provided within the elongate member 102. Further, the distal operation of the end-effector 106 through the handle 202, may include both actuating the end-effector 106 and steering it along an intended direction. The actuating members 114 may be control wires, rods, or braided cables, etc., connecting the handle 202 to the end-effector 106. When the handle 202 is operated, the actuating members 114 may be configured to push, pull or rotate the end-effector 106, to facilitate actuation and steering of the end-effector. Further, in an embodiment, multiple lumens may be provided within the elongate member 102, and each lumen may contain multiple actuating members 114.

A proximal portion of the handle 202 may have a manually operative rotatable knob configured to operate the handle 202. Further, a distal portion of handle 202 may be formed as a shank that may fit over the steering members. In addition, a linking member (not shown) may attach the handle 202 to the steering member. Such a linking member may be any appropriate fastening device, such as, a pin, clip, or a clamp device, etc. Further, based on the level of comfort and ease of handling that a user desires, while operating the end-effector 106, the handle 202 may be designed to have any appropriate shape.

Along a distal end, the medical device 200 may include the component 110, as aforementioned, depicted as being disassembled from the component 108 of the medical device 200.

Figure 4B:
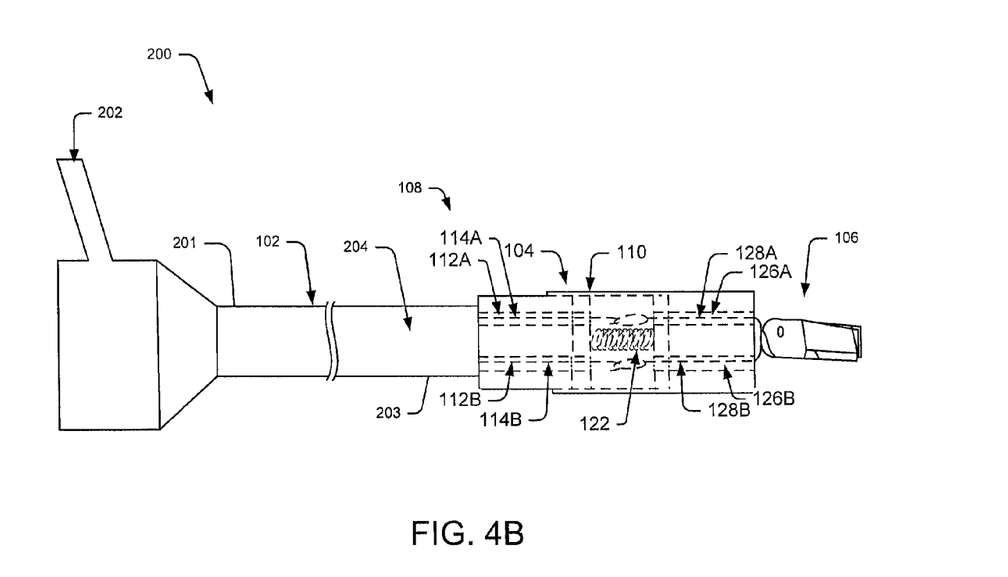
FIG. 4B is the exemplary medical device of FIG. 3A, depicting the connection system in an assembled configuration, and incorporated within the medical device, in accordance with the present disclosure.

FIG. 4B shows the medical device 200 of FIG. 4A in an assembled configuration. As shown, the end-effector 106 is shown detachably connected to a distal portion of the second component 110 of the medical device. Being in this configuration, the end-effector 106 is ready to be operated and controlled through the handle 202. Further, the end-effector 106 may also be detached from the second component 110, whenever its replacement is desired.

Embodiments of the present disclosure may be applicable to any medical or non-medical procedure. In addition, certain aspects of the aforementioned embodiments may be selectively used in collaboration, or removed, during practice, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical device, comprising:
a tubular member having a proximal end, a distal end, and at least one lumen extending therebetween;
at least one proximal control member extending within the lumen from the proximal end to the distal end of the tubular member;
a coupling mechanism removably attachable to the tubular member and removably attachable to an end effector for coupling the end-effector to the tubular member, wherein the coupling mechanism includes:
a proximal opening dimensioned to removably receive the distal end of the tubular member within the proximal opening;
a distal opening dimensioned to removably receive a proximal portion of the end effector within the distal opening; and
a plurality of plates, wherein at least one plate of the plurality of plates includes an opening for receiving the proximal control member therein; and
the end-effector, wherein the end-effector includes at least one distal control member extending proximally therefrom, and wherein the coupling mechanism is configured to removably couple the at least one distal control member to the at least one proximal control member within the coupling mechanism between the end-effector and the tubular member.

2. The medical device of claim 1, further comprising a handle operably coupled to the proximal end of the tubular member.

3. The medical device of claim 1, wherein, when the proximal control member and the distal control member are removably coupled together, the proximal control member and the distal control member are configured to cooperatively actuate the end-effector.

4. The medical device of claim 1, wherein a proximal end portion of the distal control member includes a first structure.

5. The medical device of claim 4, wherein a distal end portion of the proximal control member includes a second structure different from the first structure.

6. The medical device of claim 5, wherein one of the first and second structures is configured to receive the other of the first and second structures.

7. The medical device of claim 5, wherein the first structure includes a hook, and the second structure includes an opening configured to receive the hook.

8. The medical device of claim 1, wherein one of the plurality of plates is movable relative to the other of the plurality of plates.

9. The medical device of claim 1, wherein a resilient member is operably coupled to at least one of the plurality of plates.

10. The medical device of claim 1, wherein one of the plurality of plates is operably coupled to a cam.

11. The medical device of claim 1, wherein the at least one proximal control member includes a plurality of proximal control members, and the at least one distal control member includes a plurality of distal control members.

12. A medical device, comprising:
    a tubular member including a proximal end, a distal end, and at least one lumen extending therebetween, wherein a handle is operably coupled to the proximal end;
    a plurality of control members extending within the at least one lumen from the handle to the distal end of the tubular member, wherein the plurality of control members extend distally from the distal end of the tubular member;
    a coupling mechanism removably attachable to the tubular member and removably attachable to an end effector for coupling the end-effector to the tubular member, wherein the coupling mechanism includes:
        a proximal opening dimensioned to removably receive the distal end of the tubular member within the proximal opening;
        a distal opening dimensioned to removably receive a proximal portion of the end effector within the distal opening; and
        a plurality of plates, and wherein one of the plurality of plates is movable relative to the other of the plurality of plates; and
    the end-effector, wherein the end-effector includes a plurality of distal control members extending proximally therefrom, and wherein the plurality of control members are configured to removably couple with the plurality of distal control members at a location within the coupling mechanism between the end-effector and the tubular member.

13. The medical device of claim 12, wherein the coupling mechanism is configured to operably couple each of the plurality of control members to corresponding distal control members.

14. The medical device of claim 12, wherein at least one of the plurality of plates is coupled to a resilient member.

15. The medical device of claim 12, wherein at least one of the plurality of plates is operably coupled to a cam.

16. The medical device of claim 12, wherein a proximal end portion of at least one of the plurality of distal control members includes a first structure, and wherein a distal end portion of at least one of the plurality of control members includes a second structure different from the first structure.

* * * * *